United States Patent [19]

Overmier

[11] Patent Number: 4,510,799
[45] Date of Patent: Apr. 16, 1985

[54] METHOD OF MEASURING MATERIAL PROPERTIES OF ROCK IN THE WALL OF A BOREHOLE

[75] Inventor: David K. Overmier, Albuquerque, N. Mex.

[73] Assignee: The United States of America as represented by the United States Department of Energy, Washington, D.C.

[21] Appl. No.: 488,826

[22] Filed: Apr. 26, 1983

[51] Int. Cl.³ .................. E21B 49/02; G01N 33/24; G01N 3/02
[52] U.S. Cl. ........................ 73/151; 73/783; 73/784
[58] Field of Search .................. 73/151, 784, 783

[56] References Cited

U.S. PATENT DOCUMENTS 3,457,778  7/1969  Gill et al. .
3,992,928 11/1976  Thoms ................................. 73/783
4,155,264  5/1979  Bender ................................ 73/783

*Primary Examiner*—Howard A. Birmiel
*Attorney, Agent, or Firm*—James H. Chafin; Albert Sopp; Judson R. Hightower

[57] ABSTRACT

To measure the modulus of elasticity of the rock in the wall of a borehole, a plug is cut in the borehole wall. The plug, its base attached to the surrounding rock, acts as a short column in response to applied forces. A loading piston is applied to the top of the plug and compression of the plug is measured as load is increased. Measurement of piston load and plug longitudinal deformation are made to determine the elastic modulus of the plug material. Poisson's ratio can be determined by simultaneous measurements of longitudinal and lateral deformation of the plug in response to loading. To determine shear modulus, the top of the plug is twisted while measurements are taken of torsional deformation.

8 Claims, 3 Drawing Figures

METHOD OF MEASURING MATERIAL PROPERTIES OF ROCK IN THE WALL OF A BOREHOLE

The U.S. government has rights in this invention pursuant to Contract No. DE-AC04-76DP00789 between the U.S. Department of Energy and Western Electric Company.

BACKGROUND OF THE INVENTION

The present invention relates generally to methods for measuring properties in rock, and more particularly toward a highly sensitive, in-situ method of measuring material properties (mechanical properties) of rock surrounding a borehole.

For various scientific and economic reasons, it may be necessary to determine mechanical properties, such as elastic modulus and Poisson's ratio, in the material surrounding a borehole in rock. Mechanical properties may be of interest in scientific geologic studies. Knowledge of mechanical properties may be required in the engineering of measures to facilitate fluid flow in the rock body. Knowledge of the in-situ state of stress (the natural state of stress in the rock body) can be of critical importance in the design of subterranean structures; when the in-situ state of stress is to be determined, mechanical properties must be known in order to interpret accurately additional measured data from which the state of stress may be inferred.

The term "stress" as used herein is defined as a force acting across a unit area in rock in resisting separation, compacting or sliding that tends to be induced by external forces. "Strain" is a change in length of an object in some direction per unit undistorted length in the same or different direction. "Elastic modulus" or "modulus of elasticity" is the ratio of an increment of stress to an increment of strain. "Poisson's ratio" is the ratio of a transverse contracting (expanding) strain to the elongation (contraction) strain when a rod is stretched (compressed) by forces which are applied at its ends and which are parallel to the rod's axis. "Torsional stiffness" is the ratio of a steady torsional force acting on a rock plug to the resulting angular displacement. See generally, *Dictionary of Scientific and Technical Terms*, McGraw-Hill, 1974.

Prior art devices that are theoretically capable of remote measurements of material properties in a borehole demonstrate poor accuracy in laboratory and field tests. Typically, a relatively small piston is pressed into the wall of a borehole (see, e.g., Edmond et al U.S. Pat. No. 4,030,345) to develop a displacement signal of inherently low sensitivity. Measuring displacement across the borehole or strain in the borehole wall along an axis orthogonal to the load axis is similarly insensitive and subject to difficulties in obtaining credible data from displacement or strain transducers.

Other problems associated with prior art in-situ or remote measurement of material properties of borehole wall rock include poor repeatability in successive testing of the same sample, calibration problems due to irregularities at the piston-wall interface and poor localization of the point of measurement.

SUMMARY OF THE INVENTION

It is thus an object of the invention to provide an improved in-situ method of measuring material properties in rock.

Another object of the invention is to provide an improved in-situ method of measuring material properties in the rock surrounding a borehole.

Still another object of the invention is to provide a high sensitivity method of measuring material properties, such as elastic modulus, Poisson's ratio and torsional stiffness, in rock surrounding a borehole.

Still another object of the invention is to provide an in-situ method of measuring material properties in rock surrounding a borehole, that is repeatable and relatively insensitive to calibration errors.

Another object of the invention is to provide a method of measuring material properties in rocks surrounding a borehole at a localized position within the borehole.

To achieve the foregoing and other objects, in accordance with the purposes of the present invention as described herein, the borehole wall is cut along a closed path to form a plug having an exposed top surface and a base that is integral with underlying rock. A force is applied to the plug and the resultant deformation of the plug is measured to determine the mechanical property. Because only the material contained in the plug, rather than a larger surface of the borehole wall, is deformed by the applied force, the deformation measurement is more sensitive and has better repeatability than is provided by prior art methods.

A more specific aspect of the invention involves applying the force against the top of the plug using a piston and measuring longitudinal deformation to obtain elastic modulus. By measuring lateral as well as longitudinal deformation of the rock, Poisson's ratio is determined.

In accordance with a further aspect of the invention, the top portion of the plug is twisted, and the torsional deformation of the plug is measured to obtain torsional stiffness from which shear modulus may be inferred. Elastic and shear moduli may be combined to yield an alternate determination of Poisson's ratio.

Preferably, a circular cut is made in the rock to form a cylindrical plug. The top of the plug may be machined to a flat surface to improve repeatability by reducing aberrations at the piston-rock interface.

Still other objects of the present invention will become readily apparent to those skilled in this art from the following description wherein there is shown and described a preferred embodiment of this invention, simply by way of illustration of one of the modes best suited to carry out the invention. As it will be realized, the invention is capable of different embodiments, and its several details are capable of modifications in various, obvious aspects all without departing from the invention. Accordingly, the drawings and descriptions will be regarded as illustrative in nature and not as restrictive.

BRIEF DESCRIPTION OF THE DRAWINGS

The accompanying drawings incorporated in and forming a part of the specification, illustrate several aspects of the present invention, and together with the description serve to explain the principles of the invention. In the drawings.

DETAILED DESCRIPTION OF THE INVENTION

Figure 1:
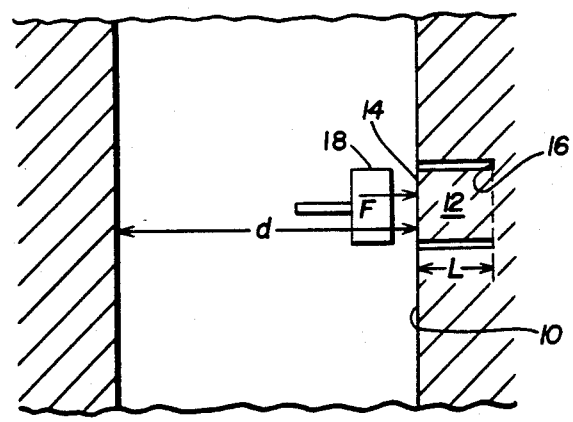
FIG. 1 is a cross-sectional, elevational view of a borehole wall cut to form a cylindrical plug for practicing the method of the invention.
Figure 2:
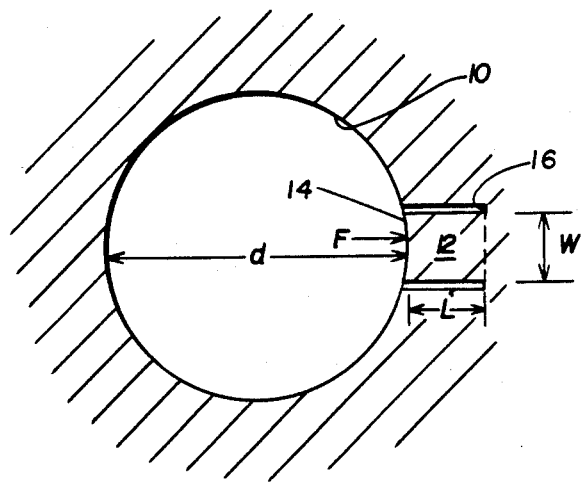
FIG. 2 is a top view of the borehole wall shown in FIG. 1.

Reference is now made to FIGS. 1 and 2 showing an improved method of the invention for measuring material properties in the rock forming the wall 10 of a borehole. A plug 12 is formed in the borehole wall 10 by making a closed cut. Preferably, a hole saw is applied at the borehole wall 10 to form a cylindrical plug 12 that has an exposed top surface 14 and a base 16 that is integral with the underlying rock. Following formation of the plug 12, a force F is applied against the top surface 14 of the plug 12 using a hydraulic jack, piston 18 or other device. Compression of the plug is measured as the plug is loaded. Simultaneous measurements of piston load and plug deformation may be monitored to provide a graph from which may be obtained a slope proportional to elastic modulus of the plug material.

Deformation of the plug as a function of applied force can be measured by any suitable means, such as by a conventional displacement gage indicating deformation relative to a suitable stationary reference, such as a diametrically opposed portion of the borehole wall, as shown in FIGS. 1 and 2.

Expressed mathematically for the most elementary case, modulus of elasticity $M=$ unit stress/unit deformation $= FL \div A\Delta d$, where F is the applied force, L is the length of the plug, $A (=(\pi/4)W^2, W=$ plug diameter) is the cross sectional area of the plug (the area to which force is applied), and $\Delta d$ is the increase in borehole diameter along the measurement axis passing through the plug. For practical purposes, this elementary calculation may be adequate. The actual case, in which the base of the plug remains attached to the rock mass from which it is cut, is readily calculated by standard finite element means. A correction may then be applied to the elementary calculation as outlined above. Further, the elementary calculation assumes uniform loading at the piston-plug interface. This is an idealization which will not be realized in practice. Finite element calculations for sample imperfect loading patterns predict only small errors from this source.

Any suitable form of displacement transducer to measure change in plug length in response to applied force can be used, including contact-type transducers such as the linear variable differential transformer and non-contacting transducers of inductance or capacitance types.

Preferably, to reduce sensitivity of the measurements to conditions at the piston-plug interface, the top of the plug may be surface machined to prevent slippage or crushing of material by the piston as force is applied against the plug. Any slippage or crushing of material, however, should be evident from inspection of a displacement vs. load record and can be compensated during data analysis. Furthermore, any deformations within the loading piston or within the displacement transducer can be calibrated out.

Although the data of primary interest are in the elastic range of the rock, as loading against the rock plug proceeds onset of inelastic behavior in the plug material will be apparent. Although only data within the elastic range of the rock are used to determine modulus, data beyond the range of elastic behavior may also be useful to determine the fracture point, or plastic behavior of the rock.

If the plug 12 is cut into a cased hole, it is not necessary to remove the remaining disc of casing material on top of the plug. The load may be applied by the piston against the top of the disc to compress the plug to obtain valid displacement information for determining elastic modulus.

Rock deflection is directly proportional to load and plug length, and is inversely proportional to modulus. For a plug 1.5 inches in diameter and 1.5 inches in length within rock having a modulus of $10\times10^6$ lbs/inch$^2$, a load of 1,000 pounds causes a measured compression in the rock of 120 microinches (as calculated by finite element means). The elementary calculation predicts for this case only 85 microinches. The finite element calculation includes the effect on the measured deformation of the plug's being rooted in the elastic rock mass.

The method of FIGS. 1 and 2 is also applicable to provide a determination of Poisson's ratio $\mu=(\Delta W/W)/(\Delta d/L)$, where $\Delta d$ is longitudinal deformation and $\Delta W$ is lateral deformation (measured across the diameter of the plug), by making simultaneous measurements of longitudinal and lateral deformations as a function of applied load.

Figure 3:
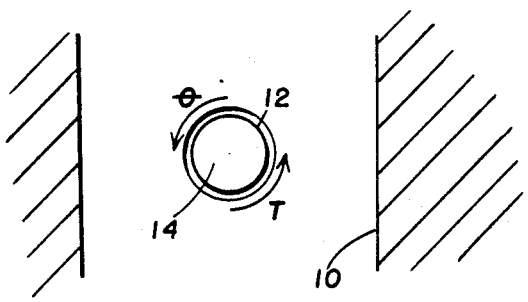
FIG. 3 is a front view of a borehole wall plug in accordance with the invention being twisted to measure torsional stiffness.

Referring to FIG. 3, torsional stiffness in the rock underlying the borehole is determined by twisting the top of the plug with torque T while measurements are taken of torsional deformation $\theta$ in a conventional manner. Although not shown for clarity, a collet may be used to grasp and twist the top of the plug, while torsional deformation measurements are made. The torque and torsional deformation may be plotted to yield a slope proportional to shear modulus. Shear modulus may be combined with elastic modulus measured in axial loading to obtain an alternate measure of Poisson's ratio.

In summary, numerous benefits have been described which result from employing the concepts of the invention. The application of longitudinal or torsional loading to a plug formed in a borehole wall, rather than to the entire wall, provides strain or displacement responses that are substantially higher than those obtained if load is applied to the undisturbed borehole wall. Furthermore, the measurements are localized at the site of the plug at a predetermined position in the borehole. Measurement errors caused by surface aberrations at the borehole wall are minimized since the primary data are in the form of slope measurements; further improvement in this respect is possible if the top of the plug is machined prior to loading.

The foregoing description of a preferred embodiment of the invention has been presented for purposes of illustration and description. It is not intended to be exhaustive or to limit the invention to the precise form disclosed. Obvious modifications or variations are possible in light of the above teachings. For example, the circular cylindrical plug has been described as the preferred embodiment since it can be conveniently formed by a hole saw. The rock can be cut along other closed paths, however, to form non-circular cylindrical plugs. Furthermore, it should be apparent that the principles of the invention are not limited to making material property measurements on rock within a borehole wall. The embodiment described herein was chosen to provide the best illustration of the principles of the invention in its practical application to thereby enable one of ordinary skill in the art to utilize the invention in various embodiments and with various modifications as are suited to the particular use contemplated. It is intended that the scope of the invention be defined by the claims appended hereto.

I claim:

1. An in-situ method of measuring elastic properties of rock surrounding a borehole, comprising the steps of cutting into a wall of the borehole along a closed path to form a plug having an exposed top surface and a base that is integral with underlying rock; applying a force to the plug; measuring resultant deformation of the plug within the elastic range of the rock and combining the applied force and resultant plug deformation to obtain a measurement of the mechanical property.

2. The method of claim 1, wherein the force is applied against the top surface of the plug.

3. The method of claim 2, wherein said mechanical property is elastic modulus and the measuring step includes measuring longitudinal deformation of the plug.

4. The method of claim 2, wherein said mechanical property is Poisson's ratio and the measuring step includes measuring longitudinal and lateral deformations of the plug.

5. The method of claim 1, wherein the mechanical property is shear modulus, the step of applying a force includes twisting a top portion of the plug and the measuring step includes measuring torsional deformation of the plug.

6. The method of claim 1, wherein the cutting step comprises making a circular cut to form a cylindrical plug in the borehole wall.

7. An in-situ method of measuring elastic modulus in the wall of a borehole, comprising the steps of measuring the diameter of the borehole along a measurement axis; cutting into the borehole wall along a closed path to form a plug having a base that is integral with the underlying rock and lies on the measurement axis; applying a force against an exposed top surface of the plug; again measuring the diameter of the borehole on the measurement axis while the force is applied to the plug within the elastic range of the rock; determining a difference between the two measured diameters and correlating the difference to elastic modulus of the borehole wall.

8. The method of claim 7, wherein said closed cut is circular to form a cylindrical plug in the borehole wall.

* * * * *